United States Patent [19]

Martin

[11] Patent Number: 5,490,652
[45] Date of Patent: Feb. 13, 1996

[54] OVERHEAD SUPPORT

[75] Inventor: Karl-Heinz Martin, Grafrath, Germany

[73] Assignee: Kreuzer GmbH + Co. OHG, Puchheim, Germany

[21] Appl. No.: 203,796

[22] Filed: Mar. 1, 1994

[30] Foreign Application Priority Data

Mar. 4, 1993 [DE] Germany .......................... 43 06 803.0

[51] Int. Cl.$^6$ ................................................ E04G 3/00
[52] U.S. Cl. ...................................... 248/282.1; 248/324
[58] Field of Search .................................. 248/282, 276, 248/283, 289.1, 285, 324, 274

[56] References Cited

U.S. PATENT DOCUMENTS

| 4,166,602 | 9/1979 | Nilsen et al. .................. 248/324 X |
| 4,953,821 | 9/1990 | Reuter et al. .................. 248/282 X |

FOREIGN PATENT DOCUMENTS

| 0330030 | 8/1989 | European Pat. Off. . |
| 2250508 | 6/1975 | France . |
| 3034013A1 | 4/1982 | Germany . |
| 3744702A1 | 12/1988 | Germany . |
| 3744706 | 12/1988 | Germany . |
| 3937518A1 | 5/1991 | Germany . |
| 9202556 | 5/1992 | Germany . |
| 2083878 | 3/1982 | United Kingdom . |
| WO-A-8805514 | 7/1988 | WIPO . |

Primary Examiner—Ramon O. Ramirez
Attorney, Agent, or Firm—Donald Brown

[57] ABSTRACT

An overhead support for carrying medical appliances and providing supply lines in the medical field comprises support arms and a support column. In order to allow a simple and cheap manufacture of such an overhead support, the support arms are made of an extruded profile having a substantially rectangular cross section, side walls, a top wall, a bottom wall, longitudinal webs extending between the top wall and the bottom wall in a direction substantially parallel to the side walls in spaced relation thereto, and a channel for the supply lines, the channel being defined by the top and bottom walls and the webs.

6 Claims, 3 Drawing Sheets

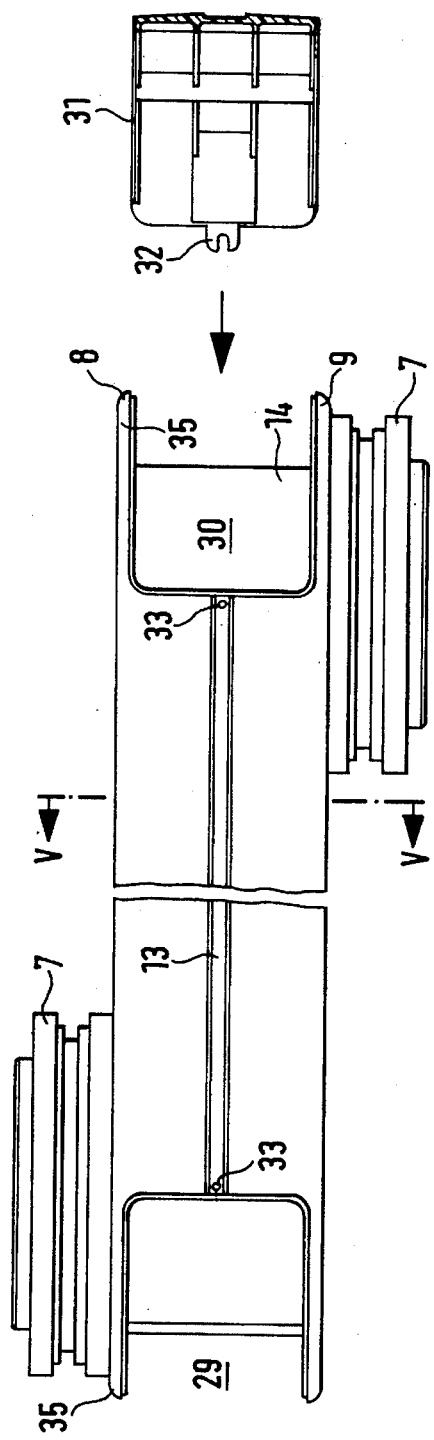
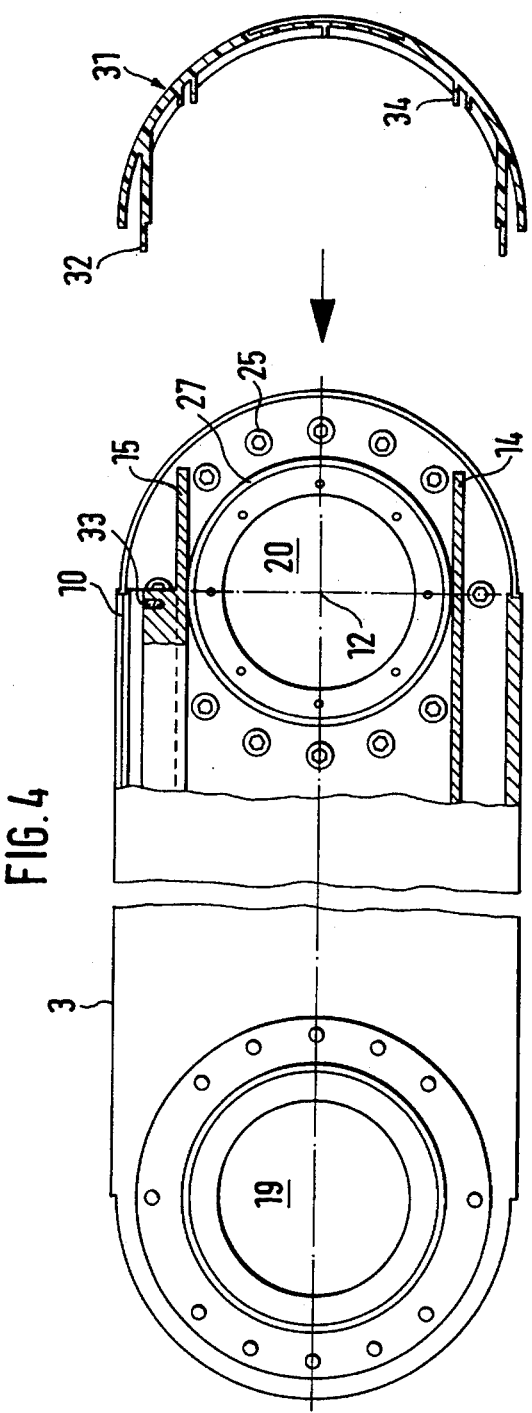

OVERHEAD SUPPORT

BACKGROUND OF THE INVENTION

The invention relates to an overhead support for carrying medical appliances. Such an overhead support comprises a ceiling mount, at least one support arm, swivel means for connecting the support arm to the ceiling mount, a column for carrying appliances or the like and supply lines for the appliances or the like within the column.

Such an overhead support is in particular used in the medical field for carrying appliances in operation rooms or the like. The support arm of known overhead supports is a cast part which renders the production of such overhead supports expensive.

OBJECTS OF THE INVENTION

It is an object of the invention to provide an improved overhead support for medical appliances, in which the above-mentioned drawback is avoided. It is a further object to provide a simple overhead support which can be manufactured in a cheap manner.

SUMMARY OF THE INVENTION

According to the invention, an overhead support comprises a ceiling mount, at least one support arm, swivel means for connecting the support arm to the ceiling mount, a column for carrying appliances or the like and supply lines for the appliances or the like within the column, the support arm comprising an extruded profile having a substantially rectangular cross section, side walls, a top wall, a bottom wall, longitudinal webs extending between the top wall and the bottom wall substantially parallel to the side walls in spaced relation thereto, and a channel for the supply lines, the channel being defined by the top and bottom walls and the webs.

BRIEF DESCRIPTION OF THE DRAWINGS

Further advantages, features and objects of the invention will stand out from the following description of an exemplary embodiment with reference to the drawings. In the drawings:

FIG. 3 is a side view of a support arm wherein the end cap is removed;

FIG. 4 is a top view of the support arm shown in FIG. 3 having the end cap removed.

DESCRIPTION OF A PREFERRED EMBODIMENT

Figure 1:
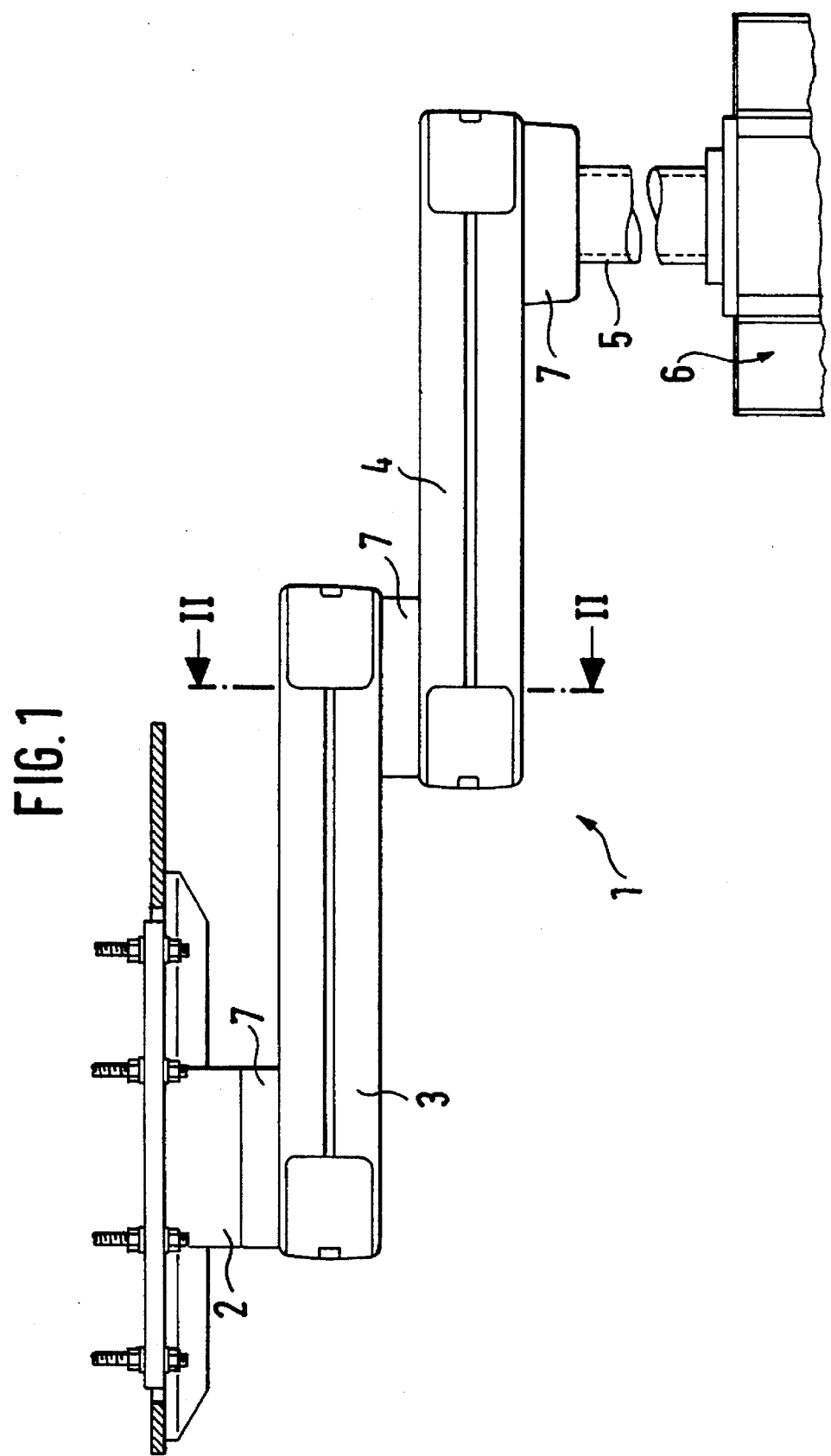
FIG. 1 is a schematic side view of an overhead support.

The overhead support 1 shown in FIG. 1 comprises in a convential manner a ceiling mount 2, a first support arm 3 connected to the ceiling mount, a second support arm 4 connected to the first support arm 3 and a column 5 connected to the second support arm for receiving loads such as medical appliances 6. Respective swivel joints 7 are provided for connecting the ceiling mount 2 with the first support arm 3, the first support arm 3 with the second support arm 4 and the second support arm 4 with a column 5.

Each support arm 3, 4 is formed as an extruded profile having a substantially rectangular cross section. The cross-sectional shape is selected so that the top wall 8 and the bottom wall 9 form the wide face of the profile and the two side walls 10, 11 form the small face. The support arms are symmetrical with respect to the center axis 12 thereof and only one side half thereof will be described below. A T-shaped groove 13 is provided substantially in the center of each of the side walls and extends parallel to the longitudinal axis of the support arm. The interior of the profiles comprises longitudinal webs 14, 15 forming straight webs extending substantially perpendicular to the top wall and bottom wall, respectively, and substantially parallel to the side walls 10, 11 in a small distance therefrom. The longitudinal webs are connected with the backside of the T-shaped groove 13 through respective longitudinal webs 16, 17 which extend substantially parallel to the top wall 8 and bottom wall 9, respectively. In this manner, a high stability of the extruded support arm 3, 4 is obtained and a channel 18 is provided in the interior thereof between the top wall 8, the bottom wall 9 and the longitudinal webs 14, 15 for passing supply lines of all kinds.

The T-grooves 13 may receive mountings in the form of (not shown) cap screws having their cap inserted into the enlarged portion of the respective groove 13 and being slidably locked therein.

As best shown in FIG. 4, the support arm 3 has a circular hole 19 at the upper side of the end thereof which is connected to the ceiling mount 2 and a circular hole 20 at the lower side of the opposite end thereof which is connected to the second support arm 4. The diameter of the holes is selected so that the holes extend across the entire width between the two facing longitudinal webs 14, 15 in order to obtain a maximum size for the passage from the channel 18 to the second support arm 4. The second support arm is of identical construction in order to ensure a corresponding passage to the column 5.

Figure 2:
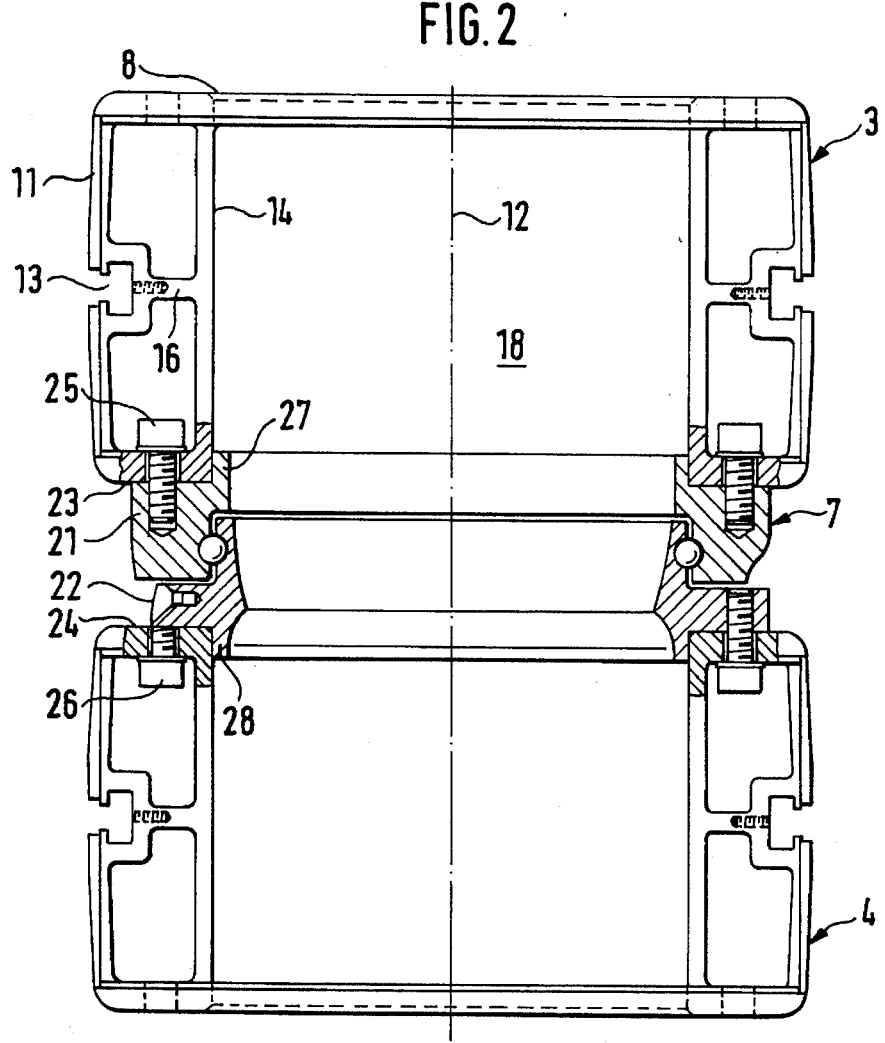
FIG. 2 is a sectional view along line II—II of FIG. 1.
Figure 5:
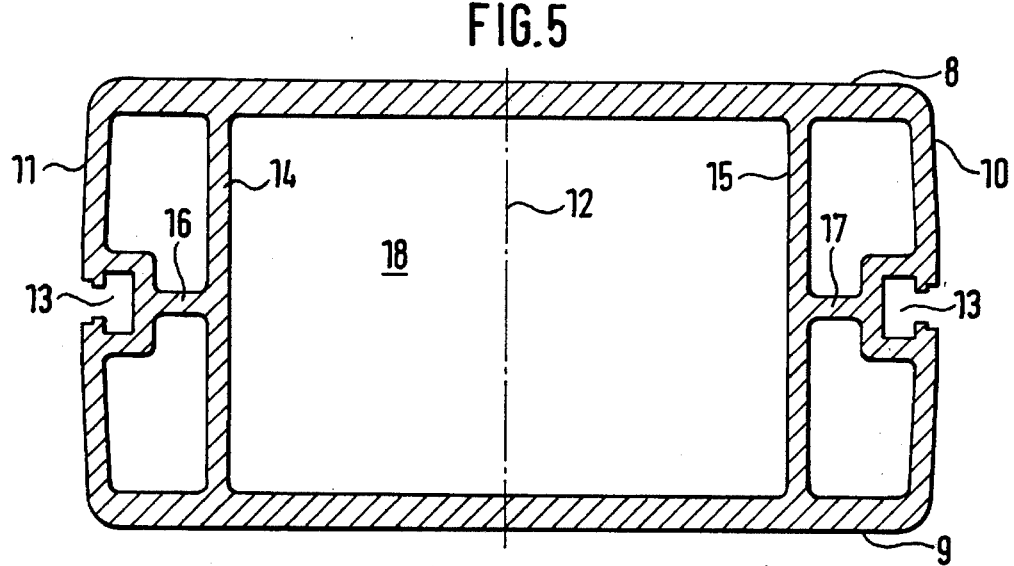
FIG. 5 is a sectional view along line V—V of FIG. 3.

Each swivel joint 7 comprises a first half bearing portion 21 connected with the part thereabove and a second half bearing portion 22 cooperating with the first half-bearing portion and being connected with the part therebelow. Both half-bearing portions 21, 22 are connected with the corresponding parts by a respective suitable screw fitting. As best shown in FIG. 2, the edge regions 23, 24 of the holes 19, 20 facing the respective half bearing portion to be connected thereto are machined to be substantially even so that the plane thereof extends perpendicular to the center axis 12. The bearing portions 21, 22 for connection thereto comprise annular abutment surfaces corresponding to the edge regions 23, 24, respectively. The abutment surfaces of the bearing portions contact the respective edge regions 23, 24, and the bearing portions are rigidly connected to the respective edge regions by means of bolts 25, 26. In addition, each bearing portion comprises a collar-shaped cylindrical section 27, 28 projecting into the respective hole 19, 20 defined by the annular edge region 23, 24. Each collar-shaped cylindrical section 27, 28 comprises an outer cylinder surface having the diameter thereof selected as a function of the diameter of the holes 19, 20 and therefore of the distance between the longitudinal webs 14, 15 so that the collar-shaped cylindrical portion of the bearing portions is connected with the corresponding edge region through a snug fit. The collar-shaped cylindrical sections receive the forces of tilt exerted by the respective support arm onto the bearing.

As best shown in the FIGS. 3 and 4, both ends of each support arm are formed semicircular with a radius corresponding to half of the width of the profile and having a center extending through the center axis 12. In this manner, apertures 29, 30 are generated at both ends and the half bearing portions, the bolts connecting those portions to the support arms and the supply lines to be passed through the respective channel and the apertures are freely accessible through the apertures 29, 30. Semicylindrical caps 31 are provided at each side for covering the apertures, one only of the caps being shown. The radius of the semicylinder corresponds to the radius of the respective ends to be covered. At both sides, the caps 31 comprise brackets 32 projecting beyond the edge thereof and each comprising a slit; the brackets are pushed into the T-groove 13 and are fastened by a bolt screwed into the threaded bolt 33. The brackets 32 together with the brackets 34 which slide onto the longitudinal webs 15 when pushing on the cap 31 ensure a stable seat of the cap at the shoulder 35 surrounding the entire aperture 30, 31 and prevent that any parts of the caps project beyond the surface of the arm so that smooth surfaces are formed all over. At the same time, the brackets 32, 34 cooperate in stabilizing the caps 31.

In this manner, a support having a high stability is provided wherein the removable end caps 31 allow for easy inspection and operations in the interior thereof. Further, the smooth surface requirements of room ventilation technology are met.

Although the invention has been described with reference to a specific example embodiment, it is to be understood that it is intended to cover all modifications and equivalents within the scope of the appended claims.

What is claimed is:

1. An overhead support comprising a ceiling mount, at least one support arm, swivel means for connecting said support arm to said ceiling mount, a column for carrying appliances supply lines for said appliances, said support arm comprising an extruded profile having a substantially rectangular cross section, side walls, a top wall, a bottom wall, longitudinal webs extending between said top wall and said bottom wall substantially parallel to said side walls in spaced relation thereto, and a channel for said supply lines, said channel being defined by said top and bottom walls and said webs.

2. The overhead support of claim 1, comprising a T-shaped groove having a base extending in at least one of said side walls in longitudinal direction of said support arm.

3. The overhead support of claim 2, wherein said profile comprises a further longitudinal web connecting the base of said T-shaped groove to the adjacent one of said longitudinal webs, said further web extending substantially perpendicular to the adjacent one of said longitudinal webs.

4. The overhead support of claim 1, comprising a second support arm and a swivel joint connecting said second support arm to said first support arm, each support arm having a hole at the place of said swivel joint and said swivel joint having two annular half-bearing portions, said half-bearing portions each having a surface for connection to the associated support arm and a collar extending substantially parallel to the center axis of said bearing for fitting to the wall of the respective hole so that forces of tilt are received.

5. The overhead support of claim 1, comprising an aperture provided at the longitudinal end of said support arm and a removable cap for closing said aperture.

6. The overhead support of claim 5, wherein said cap comprises brackets for removably engaging T-shaped grooves of said support arm and said longitudinal webs, respectively.

* * * * *